(12) United States Patent
Müller

(10) Patent No.: US 10,532,033 B2
(45) Date of Patent: Jan. 14, 2020

(54) MICRORESERVOIR SYSTEM BASED ON POLYSILOXANES AND AMBIPHILIC SOLVENTS

(75) Inventor: Walter Müller, Neuwied (DE)

(73) Assignee: LTS LOHMANN Therapie-Systeme AG, Andernach (DE)

(*) Notice: Subject to any disclaimer, the term of this patent is extended or adjusted under 35 U.S.C. 154(b) by 112 days.

(21) Appl. No.: 10/835,997

(22) Filed: Apr. 29, 2004

(65) Prior Publication Data

US 2004/0202710 A1    Oct. 14, 2004

Related U.S. Application Data

(63) Continuation of application No. 10/019,378, filed as application No. PCT/EP00/05658 on Jun. 20, 2000, now abandoned.

(30) Foreign Application Priority Data

Jul. 2, 1999   (DE) .................................. 199 30 340
Dec. 4, 1999   (DE) .................................. 199 58 554

(51) Int. Cl.
    *A61K 9/70*    (2006.01)

(52) U.S. Cl.
    CPC .......... *A61K 9/7069* (2013.01); *A61K 9/7092* (2013.01)

(58) Field of Classification Search
    None
    See application file for complete search history.

(56) References Cited

U.S. PATENT DOCUMENTS

| | | | |
|---|---|---|---|
| 3,946,106 A | | 3/1976 | Chien et al. |
| 4,036,228 A | | 7/1977 | Theeuwes |
| 4,053,580 A | | 10/1977 | Chien et al. |
| 4,573,996 A | * | 3/1986 | Kwiatek et al. .............. 424/434 |
| 4,814,184 A | | 3/1989 | Aguadisch et al. |
| 4,818,540 A | * | 4/1989 | Chien .................. A61K 9/7069 424/448 |
| 4,913,905 A | * | 4/1990 | Fankhauser et al. ......... 424/449 |
| 5,071,657 A | | 12/1991 | Oloff et al. |
| 5,145,682 A | | 9/1992 | Chien et al. |
| 5,446,070 A | * | 8/1995 | Mantelle .................... 514/772.6 |
| 5,656,286 A | * | 8/1997 | Miranda et al. .............. 424/449 |
| 5,688,523 A | * | 11/1997 | Garbe et al. .................. 424/448 |
| 5,716,636 A | | 2/1998 | Horstmann et al. |
| 5,788,983 A | * | 8/1998 | Chien et al. .................. 424/449 |
| 5,788,984 A | | 8/1998 | Guenther et al. |

(Continued)

FOREIGN PATENT DOCUMENTS

| | | |
|---|---|---|
| CA | 2326630 | 9/2000 |
| DE | 2135533 | 2/1973 |

(Continued)

OTHER PUBLICATIONS

Package leaflet: Information for the patient. (Year: 2017).*

(Continued)

*Primary Examiner* — Isis A Ghali
(74) *Attorney, Agent, or Firm* — Sterne, Kessler, Goldstein & Fox P.L.L.C.

(57) ABSTRACT

The invention relates to a transdermal therapeutic system on the basis of polysiloxane which contains microreservoirs filled with an active substance and one ambiphilic solvent.

13 Claims, 3 Drawing Sheets

(56) References Cited

U.S. PATENT DOCUMENTS

| | | | |
|---|---|---|---|
| 5,906,830 A * | 5/1999 | Farinas | A61K 9/7053 |
| | | | 424/448 |
| 6,143,319 A | 8/2000 | Meconi et al. | |
| 6,325,990 B1 | 12/2001 | Laurent | |
| 6,381,852 B1 | 5/2002 | Wallays et al. | |
| 6,521,250 B2 | 2/2003 | Meconi et al. | |

FOREIGN PATENT DOCUMENTS

| | | |
|---|---|---|
| DE | 3333240 | 3/1985 |
| EP | 0196769 | 10/1986 |
| GB | 1361289 | 7/1974 |
| HU | 73441 | 7/1996 |
| HU | 9802963 | 6/1999 |
| HU | 9902763 | 9/2000 |
| HU | 101519 | 9/2001 |
| RU | 2 044 541 | 9/1995 |
| RU | 2 140 784 | 11/1999 |
| WO | 87/07138 | 12/1987 |
| WO | 90/10425 | 9/1990 |
| WO | 94/06383 | 3/1994 |

OTHER PUBLICATIONS

Schuler, M. Th., "Aspekte der physiologischen Unbedenklichkeit beim modernen Nitrilkunststoff Barex®," Kunststofffe-Plastics, 9/74, pp. 13-20.

* cited by examiner

Fig. 3: Results of the permeation study of an estradiol/norethisterone acetate plaster as per Example 2
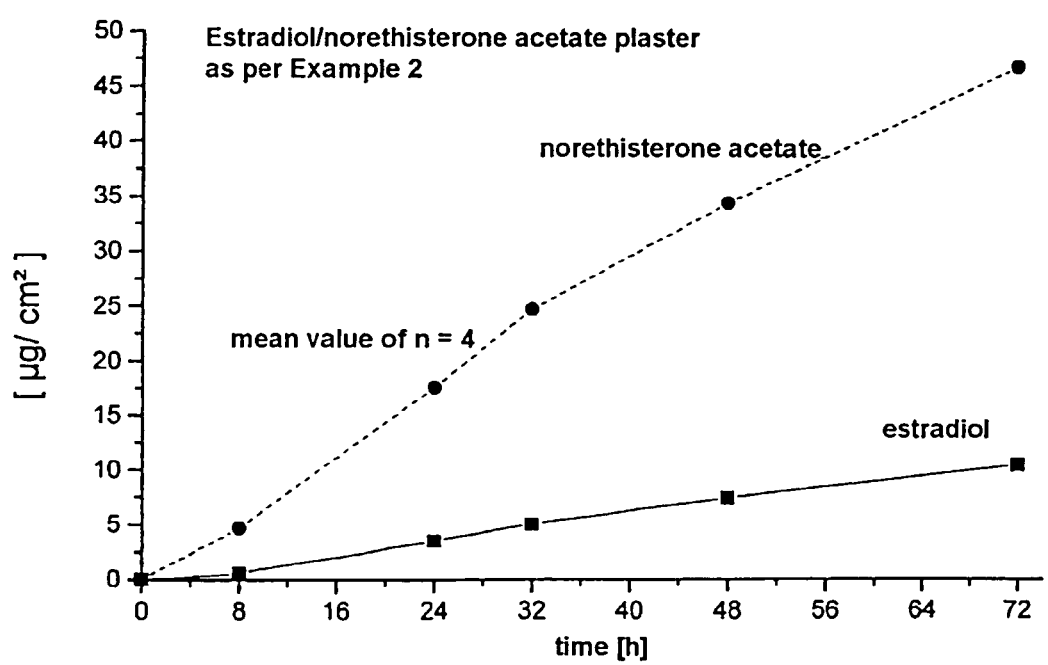

Fig. 4: Results of the permeation study of a testosterone plaster as per Example 4
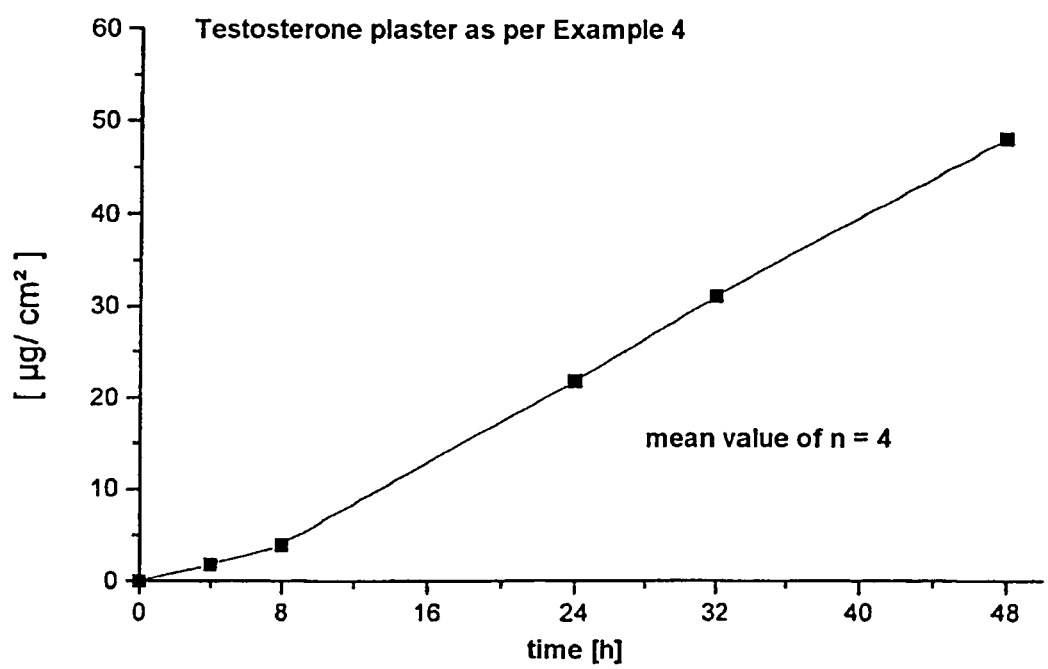

MICRORESERVOIR SYSTEM BASED ON POLYSILOXANES AND AMBIPHILIC SOLVENTS

RELATED APPLICATIONS

This application is a continuing application of application U.S. Ser. No. 10/019,378, filed Dec. 27, 2001, still pending and herein incorporated by reference, now abandoned which in turn is a 371 of PCT/EP00/05658, filed Jun. 20, 2002, and claims priority to German application Ser. Nos. 199 30 340.1, filed Jul. 2, 1999 and 194 58 554.7, filed Dec. 4, 1999.

Disregarding a few common special forms, transdermal therapeutic systems (TTS) can be differentiated into two basic types, those known as matrix systems and those known as reservoir systems.

In the case of those known as matrix systems, in the simplest case the active substance is dissolved in a self-adhesive layer or in some cases even only suspended or dispersed in the form of crystals.

The reservoir systems, which should be distinguished from the matrix systems, represent a type of pouch comprising an inert backing layer and an active substance permeable membrane, the active substance being located in a liquid preparation within this pouch. Usually, the membrane is provided with a layer of adhesive which serves to anchor the system on the skin.

BRIEF DESCRIPTION OF THE DRAWINGS

FIG. 3 shows results of a permeation study of an estradiol/norethisterone acetate plaster as per Example 2.

FIG. 4 shows results of permeation study of a testosterone plaster as per Example 4.

Figure 1:
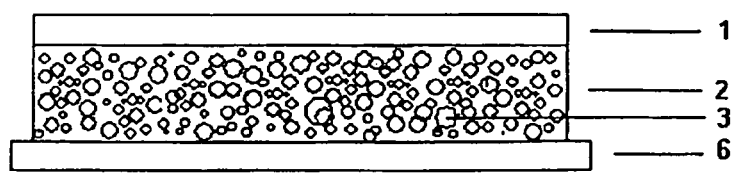
FIG. 1 illustrates a first microreservoir system.

Systems comprising liquid microreservoirs may to a certain extent be regarded as hybrids of the two basic forms. In this case as well, the active substance is located for the most part not in the polymeric constituents of the system but in the liquid microreservoirs, which are embedded into the polymer layers. In their simplest case, the liquid microreservoirs are embedded into a self-adhesive polymer layer, in which case the adhesive can itself be regarded as a kind of membrane. A system designed in this way is impossible to distinguish from a customary matrix system on the basis of just its external appearance. Only on microscopic viewing is it possible to perceive the microreservoirs and thus the heterogeneous structure of the film of adhesive. A system of this kind in its simplest embodiment is shown in FIG. 1.

Figure 2:
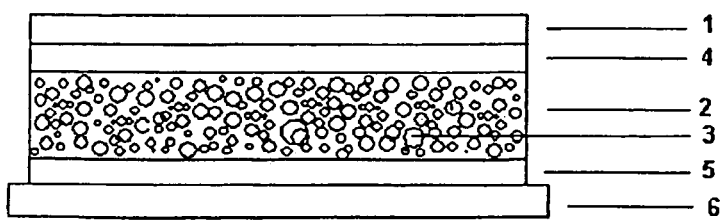
FIG. 2 illustrates a second microreservoir system.

If, however, the layer charged in this way with active substance is not self-adhesive or not sufficiently self-adhesive, a further suitable self-adhesive layer may be applied which serves to anchor the system on the skin. The same measure may then be necessary in order to improve anchoring of the backing layer of the system to the layer charged with active substance. A system of this kind, having two additional layers of adhesive, is shown in FIG. 2. Of course, with systems like this as well there is the possibility of providing the layer charged with active substance with a control membrane on the skin-facing side and then, if desired, to provide said membrane with a skin adhesive layer on the skin-facing side. This skin adhesive layer may then also be provided with microreservoirs for the purpose of delivering an initial dose.

The preferred polymer for microreservoir systems comprises polysiloxanes. Polysiloxanes have low solvency for active substances. This means that in the absence of additives the active substances in polysiloxanes are present predominantly only in dispersion and not in solution in the polymer.

Through the use of microreservoirs with physiologically acceptable solvents for the active substance to be incorporated, charging with dissolved active substance can be improved substantially.

Active substance delivery systems comprising microreservoirs are described in U.S. Pat. Nos. 3,946,106 and 4,053,580, in which polyethylene glycol, propylene glycol or 1,3-butanediol mixed with water is used as the basis for the highly hydrophilic liquid reservoirs and the polymer used is a special two-component polysiloxane which is crosslinkable in situ. The systems described in these two patents are, however, neither intended nor suitable for transdermal administration.

U.S. Pat. No. 4,814,184 describes a transdermal system based on a polysiloxane, an emulsifier based on a polyoxyethylated organopolysiloxane compound, and a polar hydrophilic active substance in solution in a hydrophilic liquid. Specifically mentioned as solvents for the hydrophilic polar active substance are polyethylene glycols having a molecular weight of between 200 and 2000. The disadvantage of this system is that an emulsifier is required, and polar hydrophilic solvents dissolve only hydrophilic polar active substances in sufficient amount. They are therefore unsuitable for active substances of moderate polarity, which precisely on account of this quality are especially suitable for transdermal administration.

U.S. Pat. No. 5,145,682 describes a system for estradiol and estradiol derivatives, alone or in combination with a gestagen, in which water-insoluble or water-immiscible permeation enhancers—n-dodecyl alcohol is mentioned specifically—are incorporated in the form of microreservoirs into a self-adhesive polymer layer. Even such highly lipophilic substances as medium- and long-chain alcohols are not good solvents for active substances of moderate polarity and thus are also not good solvents for the estradiol explicitly mentioned in this patent. Their function is therefore not to dissolve the active substance but instead merely to act as permeation enhancers and to reduce the barrier function of the stratum corneum.

It is an object of the present invention, then, to improve the charging of silicone adhesives with dissolved active substances of moderate polarity, using suitable physiologically acceptable solvents, and thus to expand the range of use of silicone adhesives and microreservoir systems.

This object is achieved in accordance with the invention by forming microreservoirs using ambiphilic, dipolar organic solvents which are preferably liquid at room temperature, which on the basis of their physicochemical properties possess limited miscibility with silicone polymers, and which in addition are miscible with water to a certain degree, preferably at least in a weight ratio of one part of solvent with 3 parts of water, e.g., 1:1.

The term "ambiphilic solvents" means, as rendered by the prefix "ambi", that these substances have a twofold philicity, namely both a certain hydrophilicity and a certain lipophilicity. They comprise, primarily, dipolar organic solvents. The miscibility with silicone polymers is judiciously not more than 20% by weight.

In terms of their properties, ambiphilic solvents are situated between the highly polar solvents such as water and the highly lipophilic solvents such as alkanes, lower fatty alcohols (having 6-12 carbon atoms), and diethyl ether. In other words, they are miscible to a certain extent with organic liquids such as ethyl acetate and hydrophilic solvents such as methanol or water, and thus possess good solvency for substances which are not too lipophilic and not too hydrophilic, i.e., active substances of moderate polarity.

The microreservoir systems produced using such ambiphilic, especially dipolar organic solvents in the context of this invention may in general terms be characterized as follows:

A transdermal therapeutic system comprising an active substance impermeable backing layer, at least one polymer layer with microreservoirs present, i.e., dispersed; therein, and at least one active substance, and a protective layer for removal before use, wherein the polymer fraction of the polymer layer consists to the extent of at least 70% by weight, preferably at least 80% by weight, of polysiloxanes, the microreservoirs contain the active substance in dissolved form, the solvent for the active substance contains at least 50% by weight, preferably at least 80% by weight, of an ambiphilic solvent, and the ambiphilic solvent is soluble in polysiloxanes to the extent of not more than about 20% by weight.

Preferably, the ambiphilic solvent is miscible with water at least in a weight ratio of one part of solvent to 3 parts of water.

The limited miscibility with polysiloxanes is based on the polar properties of the ambiphilic, especially dipolar solvents and is an important criterion, since on the one hand it permits the formation of microreservoirs and on the other hand prevents the cohesion of the films formed from polysiloxanes being unacceptably damaged as a result of excessive miscibility. A water miscibility of at least about 25% by weight, e.g., 1:1, is likewise an expression of the character of these solvents. As a result, they are able to dissolve active substances of moderate polarity, which represent the majority of the active substances suitable for transdermal use, in the necessary concentration.

Suitable solvents for the active substance may be found among compounds which are characterized in that they have at least one free hydroxyl group and at least one further ether oxygen, or at least two free hydroxyl groups.

The limited solubility in polysiloxanes (not more than 20% by weight) may be determined experimentally as follows: about 20% by weight of the test solvent, based on solids, are added to a solution of the polysiloxane; the mixture is quickly stirred and then coated onto a transparent film. The solvent of the polysiloxane is then removed at a temperature not exceeding 40° C. The film which results is subsequently investigated under the microscope for droplets of the test solvent. If droplets can be seen, this makes it certain that the solubility is below 20% by weight.

Examples of such solvents are the various butanediols, especially 1,3-butanediol, dipropylene glycol, tetrahydrofurfuryl alcohol, diethylene glycol dimethyl ether, diethylene glycol monoethyl ether, diethylene glycol monobutyl ether, propylene glycol, dipropylene glycol, carboxylic esters of triethylene and diethylene glycol, and polyoxyethylated fatty alcohols of 6-18 carbon atoms.

In order to obtain the saturation solubility ideal for the respective active substance, these solvents may also be used in blends. Ideally, the microreservoirs are free from water except for the traces of water they contain and the water which is unavoidably introduced during production. Nevertheless, it may be of advantage in specific cases to admix water, in certain amounts, to the solvent in order to reduce or increase the solubility of the active substances.

In general, these solvents have a boiling point of more than 80° C., in particular more than 110° C., under standard conditions. This is not a strict limit but it does make it easier to remove the solvent of the polysiloxane relatively selectively during the production process without at the same time stripping off the solvent of the microreservoirs in amounts which are no longer acceptable.

The ambiphilic solvents may be admixed with relatively small proportions of additives such as triglycerides and partial glycerides of medium and higher fatty alcohols and fatty acids ($C_{12}$-$C_{22}$) and with the auxiliaries mentioned later on below (except for fillers).

To produce the systems, the active substance is dissolved in the solvent or solvent mixture suitable for it and this solution is added to the solution of the polysiloxane. In addition to the ambiphilic solvent and the solvent which remains in the system, it is also possible in this case to use low-boiling solvents such as ethanol, which are subsequently removed together with the solvents of the polysiloxane. By rapid stirring, the solution of the active substance is then dispersed in the solution of the polymer. The resulting dispersion is coated onto an abhesively (dehesively) treated film, using an Erichsen coater, for example, in the desired thickness, and the solvent of the polymer is removed at temperatures of 25-100° C., preferably between 30 and 80° C. In each case, of course, the boiling point of the ambiphilic solvent should be above that of the solvent for the polysiloxane, judiciously at least 10° C., preferably at least 30° C. Subsequently, the dried film is laminated with a sheet which acts as a backing layer. The systems are then punched out. If the resulting film is not tacky or lacks adequate tack, it may be equipped by standard techniques with an additional skin adhesive layer and with an anchoring layer to the backing layer.

If it is advantageous to do so, further auxiliaries such as permeation enhancers, fillers, viscosity-influencing compounds, crystallization inhibitors or pH regulators may of course be incorporated into the system.

Permeation enhancers serve to influence the barrier properties of the stratum corneum in the sense of increasing the active substance permeability. Substances of this kind are well known to the skilled worker and the substance appropriate for the respective active substances must—if necessary—be found by means of permeation studies.

Fillers such as silica gels, titanium dioxide and zinc oxide may be used in conjunction with the polymer in order to influence certain physical parameters, such as cohesion and bond strength, in the desired way.

Viscosity-increasing substances are preferably used in conjunction with the active substance solution. Thus it has been found that dispersion of the active substance solution in the solution of the polymer is facilitated by a somewhat increased viscosity of the active substance solution, and, additionally, the dispersion increases in stability. Suitable substances for increasing the viscosity of the active substance solution are, for example, cellulose derivatives such as ethylcellulose, hydroxypropylcellulose and high molecular mass polyacrylic acids and/or their salts and/or their derivatives such as esters.

The preferred size of the microreservoirs ranges from 5-50 μm and depends essentially on the thickness of the layer containing the microreservoirs. In general, it may be stated that the maximum size of the microreservoirs should not exceed 80% of the thickness of the polymer layer. A size of between 5 and 30 μm, in particular between 10 and 25 μm, is particularly preferred, since this size is compatible with the customary thicknesses of films charged with active substance.

pH regulators are often used in conjunction with the active substance solution, since active substances having acidic or basic groups have a strongly pH-dependent solubility and permeation rate through human skin. By way of the pH, therefore, it is possible to control the delivery rate under in vivo conditions.

Since the ambiphilic solvents in the sense of this invention virtually all possess a vapor pressure which cannot entirely be ignored at room temperature, it is important that the systems do not lose any solvent in the course of storage. It is therefore important that the primary packaging is highly impervious for the solvent for the active substance and that the inner layers of the packaging material absorb this solvent only to a very limited extent. Primary packaging used for transdermal therapeutic systems comprises heat-sealable film composites in the majority of cases. Particularly suitable for these specific systems are film composites which possess a coherent aluminum foil and whose inner, heat-sealable layer is very thin and/or consists of Barex.

Barex resins, according to M. Th. Schuler "Kunststoffe-Plastics" 9/1974, pages 13-20, are thermoplastically processible barrier polymers based on acrylonitrile which are prepared by copolymerizing acrylonitrile with selected monomers and are notable for particular chemical stability. These polymers exhibit very good barrier properties to various gases such as oxygen, carbon dioxide, and nitrogen and to many chemical agents such as acids, alkalis, and solvents. Specifically, Barex is an acrylonitrile-methyl acrylate copolymer modified with a butadiene-acrylonitrile elastomer. Important Barex products are prepared by graft copolymerization of 73-77 parts by weight of acrylonitrile and 23-27 parts by weight of methyl acrylate in the presence of 8-10 parts by weight of butadiene-acrylonitrile copolymer having a butadiene content of approximately 70% by weight.

Suitable silicone polymers are supplied by various manufacturers. Polydimethylsiloxanes from Dow Corning, which are also supplied in an amine-resistant variant, have proven particularly suitable. The amine-resistant variant has no free silanol groups which in the presence of basic active substances are able to enter into further condensation reactions.

The polysiloxanes are supplied in solution form in various solvents. Solutions in low-boiling alkanes, especially n-hexane and n-heptane, have been found particularly suitable. The particular advantage of these solvents is that, as highly lipophilic nonpolar solvents, they are of only very limited miscibility with the ambiphilic, especially dipolar solvents which form the microreservoirs, and possess a sufficiently high vapor pressure to be removed at moderate temperatures, so that the ambiphilic solvent for the active substances remains in the system in a sufficient amount. As a result of the limited miscibility of the ambiphilic solvents with n-hexane and n-heptane, there are no phase separations when these solvents are removed, and the size distribution of the active-substance-charged droplets of the ambiphilic solvent that is found in the still undried composition intended for coating is approximately the same as that in the dried film.

Polysiloxanes have a certain tendency toward what is known as cold flow. By this is meant that such polymers may behave as highly viscous liquids and may emerge from the edge of the systems. This cold flow can be successfully reduced by means of fillers such as silica gel, for example.

Polysiloxanes may be self-adhesive. They are of only limited miscibility with tackifying additives. Nevertheless, it may be of advantage in an individual case to improve the tack by adding small amounts of tackifiers such as polyterpenes, rosin derivatives, or silicone oils.

Suitable materials for the backing layer include films of, for example, polyethylene, polypropylene, polyesters such as polyethylene terephthalate, a copolymer of ethylene and vinyl acetate (EVA), and polyvinyl chloride. Such films may also consist of laminates of different polymers and may further include color layers and/or color pigments. Films of this kind are well known to the skilled worker and the best film for the particular purpose can be found without problems.

Suitable materials for the removable protective film are, especially for silicone adhesives, abhesive polyethylene terephthalate films.

Systems in the sense of this invention are notable for good active substance delivery during application on the skin. This may be attributed to the fact that, while the system is being worn, the ambiphilic solvents absorb water from the skin and this water collects in the microreservoirs owing to the highly lipophilic nature of the polysiloxanes. As a result of this water uptake, the saturation solubility of the active substance in the microreservoirs is reduced, leading to a level of thermodynamic activity of the active substance that is increased or relatively constant despite delivery of active substance.

Another factor which leads to high or constant thermodynamic activity of the active substance during the application period is the fact that ambiphilic solvents in the sense of this invention are themselves absorbed transdermally. As a result, the amount of solvent still present in the system during the wearing time becomes less and thus the thermodynamic activity of the active substance is, accordingly, increased or held at a high level despite delivery of active substance.

As far as the nature of the active substance is concerned, the only real restriction is that, based on the amount necessary in terms of the dose and the intended period of use, said active substance may be incorporated into the microreservoir-equipped polysiloxane layer of the transdermal therapeutic system. Accordingly, practical considerations dictate an upper limit of a maximum daily dose of approximately 10 mg.

By way of example, the following active substances may be mentioned: hormones such as estradiol and its derivatives, gestagens such as norethisterone acetate and levonorgestrel, androgens such as testosterone and its derivatives, .beta.-blockers such as bupranolol and carvedilol, calcium antagonists such as nimodipine, nifedipine and lacidipine, ACE inhibitors such as captopril, antiemetics such as scopolamine, psycho-pharmaceuticals such as haloperidol, fluoxetine, mianserin, amitriptyline, clomipramine and paroxetine, analgesics such as buprenorphine and fentanyl, antiasthmatics such as salbutamol and tulobuterol, antiparkinsonian agents such as biperiden and selegiline, muscle relaxants such as tizanidine, antihistamines such as dimethindene, doxylamine, alimemazine and carbinoxamine.

In summary, it may be stated that systems in the sense of this invention are advantageously suited to the transdermal administration of active substances of moderate polarity with a daily dose which does not exceed approximately 10 mg.

In the examples below, the preparation of a number of typical systems is described. With some systems, prepared as described in Examples 2 and 4, in vitro permeation studies were carried out using human epidermis and Franz diffusion cells, which are known to the skilled worker. The results of these studies are depicted graphically in FIGS. 3 and 4.

EXAMPLE 1

1.0 g of estradiol hemihydrate is dissolved in 10.0 g of diethylene glycol monoethyl ether. This solution is dispersed by rapid stirring in 55.0 g of an amine-resistant polydimethylsiloxane (BIO-PSA 4201 from Dow Corning; 73% solids content). This composition is coated in a thickness of 400 μm onto an abhesive polyethylene terephthalate film (Scotchpak 1022 from 3M) using an Erichsen coater and the solvent is removed by drying at approximately 45° C. for 20 minutes.
The dried film is laminated with the backing layer (Scotchpak 1220 from 3M). The plasters are punched out and sealed into pouches of the primary packaging material.

EXAMPLE 2

0.05 g of estradiol hemihydrate and 0.5 g of norethisterone acetate are dissolved in 4.5 g of diethylene glycol monoethyl ether. This solution is dispersed by rapid stirring in 20.5 g of an amine-resistant polydimethylsiloxane (BIO-PSA 4301 from Dow Corning, 73% solids content). This composition is coated in a thickness of 400 μm onto an abhesive film (Scotchpak 1022) using an Erichsen coater and the solvent is removed by drying at approximately 45° C. for 20 minutes. The dried film is finally laminated with the backing layer (Scotchpak 1220).

BIO-PSA 4301 is coated in a thickness of 50 μm onto an abhesive film (Scotchpak 1022) and the solvent is removed by drying at approximately 45° C. for 20 minutes. Then the protective film (Scotchpak 1022) is removed from the active-substance-charged film which was produced first and the film is laminated onto the pressure-sensitive adhesive layer for the skin that was prepared in the second step. The plasters are then punched from the resulting overall laminate and are sealed into pouches of the primary packaging material.

EXAMPLE 3

1.0 g of bupranolol is dissolved in 3.0 g of tetrahydrofurfuryl alcohol. This solution is dispersed by rapid stirring in 21.9 g of a BIO-PSA 4301 solution (73% solids content). This composition is coated in a thickness of 400 μm onto an abhesive film (Scotchpak 1022) using an Erichsen coater and the solvent is removed by drying at approximately 45° C. for 20 minutes. The dried film is laminated with the backing layer (Scotchpak 1220). The plasters are punched out and sealed into pouches of the primary packaging material.

EXAMPLE 4

1.0 g of testosterone, 1.0 g of nicotinamide and 0.4 g of oleic acid are dissolved in 6.2 g of diethylene glycol monoethyl ether and 6.2 g of 1,3-butanediol. This solution is dispersed by rapid stirring in 60 g of a BIO-PSA 4201 solution (73% solids content). This composition is coated in a thickness of 400 μm onto an abhesive film (Scotchpak 1022) using an Erichsen coater and the solvent is removed by drying at approximately 45° C. for 20 minutes. The dried film is finally laminated with the backing layer (Scotchpak 1220).

BIO-PSA 4301 is coated in a thickness of 50 μm onto an abhesive film (Scotchpak 1022) and the solvent is removed by drying at approximately 45° C. for 20 minutes. Then the protective film (Scotchpak 1022) is removed from the active-substance-charged film which was produced first and the film is laminated onto the pressure-sensitive adhesive layer that was prepared in the second step. The plasters are then punched from the resulting overall laminate and are sealed into pouches of the primary packaging material.

In FIGS. 1 to 4, the numerals have the following meanings:
(1)=backing layer
(2)=polymer layer
(3)=active substance microreservoirs
(4)=anchoring layer
(5)=skin adhesive layer
(6)=protective layer

The invention claimed is:

1. A transdermal therapeutic system consisting essentially of:
   an active substance impermeable backing layer comprising polyethylene terephthalate;
   at least one polymer layer with microreservoirs present therein;
   an optional self-adhesive layer adjacent to the at least one polymer layer for anchoring the therapeutic system to skin;
   an optional self-adhesive, microreservoir-free layer adjacent to the at least one polymer layer for anchoring the therapeutic system to the backing layer;
   bupranolol as the active substance, wherein the active substance is dissolved in a solvent in said microreservoirs; and
   a protective layer for removal before use;
   wherein:
   a) at least 70% by weight of the polymer in the polymer layer consists of at least one amine-resistant polysiloxane that is soluble in lipophilic solvents;
   b) the microreservoirs are essentially free of water and wherein the solvent in which the active substance is dissolved, consists of at least 50% by weight of an amphiphilic solvent selected from the group consisting of diethylene glycol monoethyl ether, diethylene glycol dimethyl ether, tetrahydrofurfuryl alcohol, dipropylene glycol, and mixtures thereof; and wherein
   c) the amphiphilic solvent is soluble in polysiloxanes to the extent of not more than about 20% by weight.

2. The transdermal therapeutic system of claim 1, wherein at least 80% by weight of the polymer in the polymer layer consists of at least one amine-resistant polysiloxane.

3. The transdermal therapeutic system of claim 1, wherein the solvent consists of at least 80% by weight of an amphiphilic solvent.

4. The transdermal therapeutic system of claim 1, wherein the polysiloxane is self-adhesive.

5. The transdermal therapeutic system of claim 1, wherein the maximum size of the microreservoirs does not exceed 80% of the thickness of the polymer layer; and wherein the microreservoirs have an average diameter of 5-50 μm.

6. The transdermal therapeutic system of claim 5, wherein the microreservoirs have an average diameter of 5-30 μm.

7. The transdermal therapeutic system of claim 1, wherein at least 80% by weight of the polymer in the polymer layer consists of at least one amine-resistant polysiloxane; and wherein the solvent consists of at least 80% by weight of an amphiphilic solvent.

8. The transdermal therapeutic system of claim 1, wherein the amphiphilic solvent is selected from the group consisting of diethylene glycol monoethyl ether, diethylene glycol dimethyl ether, tetrahydrofurfuryl alcohol, dipropylene glycol, and mixtures thereof.

9. The transdermal therapeutic system of claim 8, wherein the amphiphilic solvent is selected from the group consisting of diethylene glycol monoethyl ether, tetrahydrofurfuryl alcohol, and a mixture thereof.

10. The transdermal therapeutic system of claim 8, wherein the amphiphilic solvent is selected from the group consisting of diethylene glycol dimethyl ether, dipropylene glycol, and a mixture thereof.

11. The transdermal therapeutic system of claim 1, wherein the amphiphilic solvent is diethylene glycol dimethyl ether.

12. The transdermal therapeutic system of claim 1, wherein the self-adhesive layer adjacent to the at least one polymer layer for anchoring the therapeutic system to skin is not optional.

13. The transdermal therapeutic system of claim 1, wherein the self-adhesive, microreservoir-free layer adjacent to the at least one polymer layer for anchoring the therapeutic system to the backing layer is not optional.

* * * * *